United States Patent [19]

Suciu et al.

[11] Patent Number: 4,634,796

[45] Date of Patent: Jan. 6, 1987

[54] PRODUCTION OF HIGH PURITY PHENOL

[75] Inventors: George D. Suciu, Ridgewood; Ali M. Khonsari, Bloomfield, both of N.J.

[73] Assignee: Lummus Crest, Inc., Bloomfield, N.J.

[21] Appl. No.: 715,884

[22] Filed: Mar. 25, 1985

[51] Int. Cl.⁴ ............................................. C07C 37/76
[52] U.S. Cl. ..................... 568/757; 568/749; 568/754; 203/34; 203/36
[58] Field of Search ............... 568/749, 754, 757; 203/34, 36

[56] References Cited

U.S. PATENT DOCUMENTS

| | | | |
|---|---|---|---|
| 2,864,869 | 12/1958 | Croker et al. | 568/754 |
| 2,992,169 | 12/1961 | Gregory et al. | 568/754 |
| 3,029,293 | 12/1962 | Nixon | 568/754 |
| 3,029,294 | 12/1962 | Keeble | 568/754 |
| 3,102,149 | 8/1963 | Barry | 568/754 |
| 3,140,318 | 7/1964 | Sodomann et al. | 568/754 |
| 3,322,651 | 5/1967 | Nielsen | 568/754 |
| 3,672,961 | 6/1972 | Nixon | 568/754 |
| 3,692,845 | 9/1972 | Cheema et al. | 568/754 |
| 3,996,111 | 12/1976 | Hanotier | 568/754 |
| 4,016,213 | 4/1977 | Yeh et al. | 568/754 |
| 4,298,765 | 3/1981 | Cochran | 568/754 |

FOREIGN PATENT DOCUMENTS 0055329  5/1981  Japan ................ 568/754

Primary Examiner—Werren B. Lone
Attorney, Agent, or Firm—Elliot M. Olstein

[57] ABSTRACT

Phenol feed to a steam distilling column, containing alpha-methylstyrene and mesityl oxide, is treated with a base, without acidification, and the heavy phenol product is acidified and distilled in a high purity column to recover high purity phenol as a sidestream and lighter components as overhead. Acidification after steam distilling, rather than prior to steam distilling, increases phenol recovery by reducing the overhead pasteurizing cut from the high purity column.

14 Claims, 1 Drawing Figure

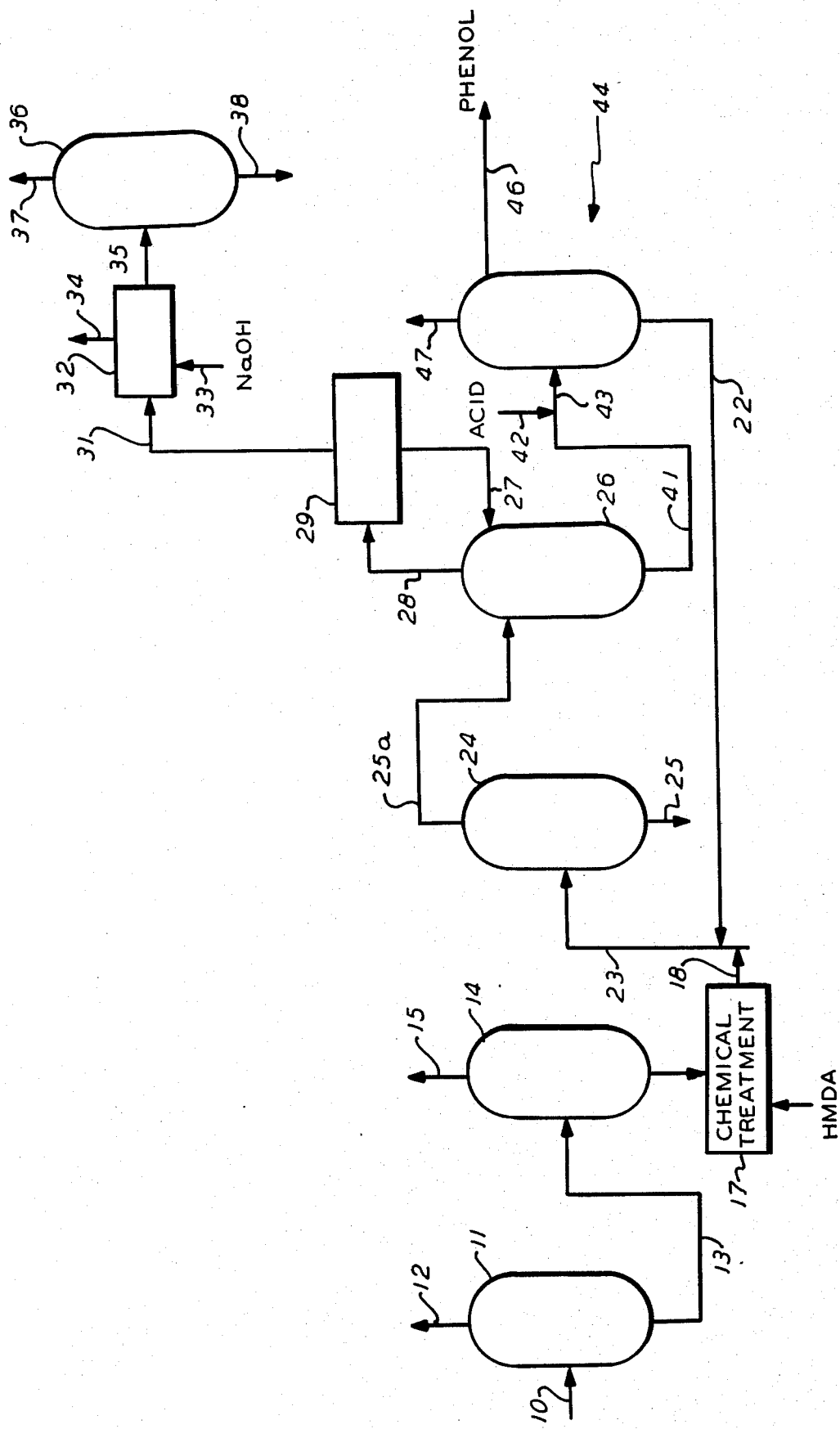

PRODUCTION OF HIGH PURITY PHENOL

This invention relates to the production of phenol, and more particularly, to the production of high purity phenol.

Phenol may be produced from cumene by the oxidation of cumene to cumene hydroperoxide, followed by cleavage of the hydroperoxide to phenol and acetone. Such a process is generally referred to as the "cumene process".

In the "cumene process", the reaction product is introduced into a separation and recovery system wherein the crude product is initially treated in a distillation column to separate acetone byproduct from the remaining mixture. The acetone-free product is then introduced into a further distillation column which operates to separate cumene from the remaining product. Optionally, the cumene recovery column can be operated to recover alpha-methylstyrene (AMS) with the cumene. If the AMS is not recovered with the cumene, the product remaining from the cumene column is introduced into a crude AMS column to separate AMS from the remaining mixture.

The product remaining from the cumene recovery column, or the crude AMS column (in the case where AMS is recovered separately from the cumene), is then introduced into a phenol recovery column to separate phenol from remaining higher boiling components.

The thus recovered crude phenol includes impurities such as acetol, mesityl oxide (MO), acetophenone, 2- and 3- methyl-benzofurans (collectively or individually methylbenzofuran or MBF), etc.

In one process, the crude phenol is chemically treated to reduce the amount of acetol and MO present in the crude phenol. Thus, for example, the crude phenol may be treated with a base, such as an amine, followed by the addition of acid or acid anhydride, as disclosed, for example, in U.S. Pat. No. 3,692,845.

The resulting product is referred to as a resin or "ONE" grade phenol.

U.S. Pat. No. 4,298,765 describes a procedure for recovering a high purity phenol wherein, after treatment with base, and an acid or acid anhydride, the treated phenol is steam distilled to recover from the top of the column a phenol-water azeotrope which contains the majority of the MBF and other impurities initially present in the treated phenol. Water present in the azeotrope is treated to separate MBF and other impurities so as to enable recycle of such water to the distillation. A heavy product, containing phenol, is recovered from the steam distillation, and the heavy product is subjected to distillation to recover high purity phenol.

In U.S. application Ser. No. 547,403, filed on Oct. 31, 1983, there is disclosed a process for recovering high purity phenol wherein a phenol product recovered from the process includes AMS produced as byproduct in the process, and optionally, some cumene. After treatment with a base, such as amine, followed by treatment with acid or acid anhydride, the phenol is subjected to steam distillation to recover the AMS, MBF and other impurities as a light product, and a heavy product containing phenol, which is then subjected to distillation to recover high purity phenol. As described in such application, the presence of AMS during the steam distillation, and optionally, also some cumene, reduces the amount of water required in the steam distillation, which in turn, reduces the amount of phenol which is present in the light product from the steam distillation.

In accordance with one aspect of the present invention, there is provided a process for producing high purity phenol wherein a phenol product, which contains alpha-methylstyrene byproduct, and methylbenzofuran, as an impurity after treatment with a base, without acidification, is subjected to steam distillation to recover a light product containing phenol, water, AMS and MBF, and a heavy product containing phenol with a reduced quantity of MBF. The heavy product is then treated with an acid and subjected to distillation to recover high purity phenol (high purity column).

The present process is based, in part, on applicant's discovery that when a phenol product is steam distilled in the presence of alpha-methylstyrene, after chemical treatment with a base and acidification, although there is essentially no AMS present in the heavy product recovered from the steam distillation, the light product, which is recovered from the subsequent distillation of the heavy product from the steam distillation, contains significant quantities of AMS, which necessitates an increase in the amount of the pasteurizing fraction recovered from such distillation so as to reduce and/or eliminate the presence of AMS in the high purity phenol product.

Although the present invention is not limited to any reasoning, it is believed that if the phenol containing AMS, which is subjected to steam distillation, is acidified after treatment with a base, the AMS reacts with itself or phenol to produce high boilers, which are recovered in the heavy product from the steam distillation. In the subsequent distillation of such heavy product, it is believed that such AMS-derived compounds decompose in the lower part of such distillation column (high purity phenol column) to produce AMS, which concentrates in the high purity phenol fraction. As a result, in accordance with the present invention, the phenol feed to the steam distillation is treated with a base without acidification so as to prevent the presence of AMS-derived heavy products in the heavy product recovered from the steam distillation.

Applicant has further found that if the feed to the steam distillation is treated with a base without acidification then the high purity phenol product which is recovered by distilling the bottoms from the steam distillation in the high purity column includes discoloring components, which give the high purity phenol product a pink-brown color. Applicant has found that, if the heavy product from the steam distillation, which is the feed to the high purity column, is treated with an acid, the high purity phenol product does not include such discoloring components; i.e., the high purity phenol is essentially colorless.

Thus, in accordance with the present invention, it is possible to obtain the advantages of having AMS present in the steam distillation column, without the necessity of increasing the pasteurizing cut recovered from the high purity column, while still recovering a colorless high purity phenol product. Such a result is achieved by omitting the acid neutralization which conventionally follows the chemical treatment with a base, preferably an amine, and by acidifying the heavy product from the steam distillation which is the feed to the high purity column.

More particularly, phenol which is subjected to chemical treatment with a base, preferably an amine, such as hexamethylenediamine, is not treated with acid or acid anhydride prior to the steam distilling. Thus, the feed to the steam distillation is not at acidic conditions. In most cases, the feed is at basic conditions as a result of excess base in the feed; i.e., base which is not consumed in the chemical treatment.

The bottoms product from the steam distilling is then treated with an acid to neutralize any amine and provide acidic conditions for the feed to the high purity column.

The pH of the feed to the steam distilling and of the heavy product feed to the high purity column may be conveniently measured as a 5% aqueous solution; i.e., dilution of the feed with water. In general, the pH of the chemically treated feed to the steam distilling, as measured for a 5% aqueous solution, is at least 6.5, and preferably at least 7.0, with the pH in most cases not exceeding 8.0.

The acidified heavy product (acidified with a suitable acid or anhydride such as phthalic acid, phthalic anhydride, phosphoric acid, etc.) is generally at a pH of no greater than 5.5, with the pH generally being no lower than 2.0; preferably no lower than 3.0, all maasured as a 5% aqueous solution of the feed to the high purity comumn.

In accordance with one aspect of the present invention, in a process for producing phenol by oxidation of cumene to cumene hydroperoxide, followed by cleavage of cumene hydroperoxide to phenol and acetone, there is recovered a crude phenol, which contains AMS and optionally, some cumene, as well as impurities comprising MBF, mesityl oxide, acetol and higher boiling impurities. Such crude phenol is treated with an amine to reduce the quantity of acetol and mesityl oxide. Subsequent to the amine treatment, phenol which still contains AMS (and some cumene if the cumene was present in the crude phenol) and impurities comprising MBF, without neutralization, is subjected to distillation in the presence of water (steam distillation) to recover a heavy product comprising phenol, containing a reduced amount of MBF, and a light product, containing water, AMS and any cumene which is added to the column with the phenol feed. Prior to the steam distillation (either before or after, preferably after treatment with the amine), high boiling components are separated from the phenol by a coarse distillation.

The AMS maintained in the phenol introduced into the column can function as an extraction solvent in the condensed overhead recovered from the column. In addition, the presence of AMS (and generally also some cumene) in the steam distillation column permits a reduction in the amount of water required in the column, which reduces the amount of phenol recovered in the light product. Thus, the presence of the AMS in the column permits a reduction in the ratio of water to phenol used in the steam distillation column, as compared to such steam distillation in the absence of AMS in the column.

As a result of maintaining AMS byproduct in the phenol product introduced into the distillation column, it is possible to separate MBF in the overhead fraction by use of a weight ratio of water to phenol which is as low as 0.05:1, preferably at least 0.1:1. In general, such a result can be accomplished with a water to phenol ratio which does not exceed 0.8:1, and generally does not exceed 0.5:1.

The amount (weight) of AMS and cumene or AMS alone (solvent) required in order to perform separation of the MBF with reduced water, is a multiple of the amount (weight) of the MBF present. For the range of MBF concentrations usually present in the crude phenol (30–200 ppm), the solvent is generally employed in an amount of at least 0.5%, with the solvent amount generally not exceeding 10%, and most generally not exceeding 7%, all by weight, based on phenol.

The amount of solvent employed should be minimized consistent with the effective removal of impurities in the light product in that an increase in the amount of solvent will necessitate an increase in the amount of water in the column, which results in a corresponding increase in the amount of phenol in the light product.

As hereinabove indicated, the AMS byproduct, and optionally, also some cumene, is maintained in the phenol product fed to the steam distillation. More particularly, the phenol fed to the steam distillation is initially derived from the cumene recovery column which is in the separation and recovery section of the phenol production plant, and the subsequent chemical treatment of such crude phenol with a base to reduce the content of acetol and MO is effected in a manner such that the AMS (and generally some cumene) which is present in the crude phenol subjected to such chemical treatment, remains in the chemically treated phenol. For example, the AMS and optionally, cumene, may be retained in the chemically treated phenol by operating under reflux conditions.

The water and solvent, as well as the water and phenol, are recovered as azeotropes in the overhead product, along with the impurities, from the steam distillation. It has been found that a heavy product (bottoms) of phenol can be recovered which is essentially free of solvent and water and which contains MBF in an amount no greater than 10–25 ppm, as compared to an MBF content in the feed in the order of 50–200 ppm.

The overhead product from the steam distillation column is condensed, and the condensed product is separated into an organic and an aqueous phase. The separated aqueous phase may be recycled to the distillation. Appropriate amounts of makeup water are added to the recycle in order to compensate for the water which may have dissolved in the organic phase.

The separated organic phase, which contains the solvent (AMS alone or AMS and cumene), MBF and other impurities, and some phenol, after separation from the aqueous phase, may be treated in any of the known ways, such as with a base (for example, sodium hydroxide) to recover any phenol present therein in an aqueous phase in which the phenol dissolves as a phenate. Such water soluble phenate may be subjected to a "springing" operation, as known in the art, in order to recover the phenol.

The steam distillation of crude phenol is generally accomplished in a distillation column, when operated at approximately atmospheric pressure, to have an overhead temperature of from 98° C. to 99° C. and a bottoms temperature from 182° C. to 185° C. The operating pressure can be atmospheric, or either higher or lower than atmospheric pressure, without departing from the teaching of the invention (the overhead temperature is the boiling temperature of the azeotrope at the prevailing pressure). It should be understood that the overhead and bottoms temperatures will vary with the pressure employed, moisture and amount of solvents used.

The composition of the product recovered at the top of the steam distillation column corresponds or is close to that of mixtures of the azeotropes formed from the phenol, solvent and water at the operation pressure.

The heavy product which is recovered from the steam distillation column, which includes phenol, includes heavier components, and in accordance with the procedure of the present invention, such heavy product is acidified prior to being introduced into a high purity column. In the high purity column, heavy components are recovered as bottoms, and the high purity phenol is recovered as a sidecut, with a pasteurizing cut being recovered from the top of the column so as to insure that the high purity phenol product has a low quantity of lighter components. By proceeding in accordance with the present invention wherein, subsequent to the amine treatment, and prior to the steam distillation, the amine is not neutralized, followed by neutralization of the amine subsequent to the steam distillation, and prior to distillation in the high purity column, there can be recovered a colorless, high purity phenol from the high purity column, without significantly increasing the amount of pasteurizing cut recovered from the high purity phenol column.

The present invention will be further described with respect to the accompanying drawing wherein:

The drawing is a simplified schematic representation of an embodiment of the present invention.

It is to be understood, however, that the scope of the invention is not limited to the preferred embodiment.

Referring now to the drawing, a reaction effluent recovered from the reaction section of a procedure for producing phenol by the oxidation of cumene to cumene hydroperoxide, followed by acid cleavage of the hydroperoxide to phenol and acetone, in line 10, includes, as principal components, phenol, acetone, cumene, alphamethylstyrene and, as primary impurities, MBF, acetophenone, acetol, MO, etc., is introduced into an acetone recovery column, schematically designated as 11, which is operated so as to recover acetone as an overhead through line 12, and a remaining bottoms product through line 13.

The bottoms product in line 13, is introduced into a cumene recovery column, generally designated as 14, operated at conditions to recover cumene and AMS as overhead through line 15. The cumene recovery column 14 is specifically operated in a manner such that there is AMS present in the bottoms product recovered through line 16 for use, as hereinafter described, in the procedure of the present invention directed to separation of MBF from phenol. In general, there is also some cumene in the bottoms product.

The bottoms in line 16 includes phenol, as well as cumene and AMS, and as impurities, MO, MBF, acetol and acetophenone, etc.

The bottoms in line 16 is then introduced into a chemical treatment zone, schematically generally indicated as 17, wherein the bottoms is treated with an amine to reduce the quantity of acetol and MO in the crude phenol. The amine is preferably hexamethylenediamine. The chemical treatment is effected in a manner such that acetol and MO are converted to higher boiling components. In accordance with the present process, chemical treatment is accomplished in a manner such that the cumene and AMS remain in the liquid phase, as compared to the prior art procedure wherein cumene and AMS concentrate in the vapor phase and are removed from the crude phenol product.

The chemically treated phenol from chemical treatment zone 17, in line 18 is combined with heavier components, in line 22, obtained as hereinafter described, and the combined stream in line 23 is introduced into a column, schematically generally indicated as 24, in which a coarse distillation operation is performed, in order to separate higher boiling components, from the crude phenol stream introduced through line 23. As hereinabove indicated, the acid addition is eliminated.

The heavier components recovered from column 24 through line 25 may then be further treated by procedures known in the art, in order to recover more of the phenol contained therein.

The overhead stream recovered from column 24 through line 25a includes phenol, as well as cumene and AMS, which will function as the organic solvent in the subsequent distillation, and as impurities, MBF, small amounts of MO, some acetone and other impurities. The crude phenol in line 25a is essentially free of materials which boil higher than acetophenone. The crude phenol in line 25a is introduced into the upper portion of an azeotropic distillation column, schematically generally indicated as 26, along with an aqueous phase, in line 27, obtained as hereinafter described. The feed to column 26, as hereinabovd described, has not been acidified so as to neutralize the amine.

The column 26 is provided with a suitable known means for effecting heating thereof, such as a side boiler (not shown). Alternatively, live steam may be introduced into the azeotropic column 26.

The column is operated at a temperature and pressure to separate impurities from phenol, e.g., the conditions hereinabove described. Azeotropes, which include water, phenol, the cumene-AMS solvent and impurities, such as MBF and the like, are recovered from the top of the column through line 28.

The overhead in line 28 is cooled (not shown) in order to effect condensation thereof. The condensed overhead is introduced into a separation zone, schematically generally indicated as 29 to separate the condensed overhead into an aqueous phase and an organic phase.

The aqueous phase, which is comprised of phenol and water, and which contains a reduced amount of impurities, is recycled to the column 26 through line 27.

The separated organic phase, comprised of the AMS and cumene, which function as an extraction solvent, as well as phenol, and impurities, including MBF, is withdrawn from the separation zone 29 through line 31, and introduced into zone 32, wherein the organic phase is contacted with aqueous base, such as sodium hydroxide, introduced through line 33 for the purpose of converting any phenol to sodium phenate, which is water soluble, while MBF and other impurities are not, whereby they remain in the organic solvent. Such recovery of phenol from an organic phase is well known in the art, and no further details are required for a complete understanding of the present invention.

Aqueous sodium phenate is recovered from zone 32 through line 34 for subsequent treatment to recover phenol.

The organic phase, which is now essentially free of phenol, is withdrawn from zone 32 through line 35 for further treatment, as required, in order to recover cumene therefrom, for recycle, as feed to the phenol production. For example, as shown in the drawing, the organics in line 35 are introduced into a distillation column 36 operated to recover cumene as overhead through line 37, and AMS and heavier components, including MBF and other impurities, as a bottoms, through line 38. The bottoms in line 38 may be further treated, as desired.

Phenol bottoms recovered from the azeotropic steam distillation column through line 41, which is essentially free of AMS and heavy components formed from AMS, is acidified with acid added through line 42 so as to neutralize any amine present in the phenol bottoms in line 41 and also to eliminate any discoloring components. The acid in line 42 may be a suitable acid of the type used is prior art processes for neutralizing the phenol product imediately after chemical treatment with a base. The acid is preferably phthalic anhydride.

The acidified heavy product in line 43 is introduced into a high purity column, generally indicated as 44 for recovering high purity phenol. The high purity column 44 is operated at conditions generally known in the art to recover heavy components as a bottoms through line 22, and high purity phenol as a sidecut through line 46. A pasteurizing cut is recovered from the top of the column through line 47 so as to reduce and/or eliminate the presence of lighter components in the high purity phenol product. As hereinabove indicated, by proceeding in accordance with the present invention, wherein the amine is not neutralized prior to the steam distillation column and acid is added to the feed to the high purity column, the amount of the pasteurizing cut, recovered through line 47, may be reduced. The pasteurizing cut recovered through line 47 may be recycled to the "front end" of the process, as generally practiced in the art.

In accordance with a preferred embodiment, the high purity phenol recovered from column 44 through line 46 contains less than 30 ppm of MBF, and preferably less than 15 ppm of MBF, with the total impurities generally not exceeding 50 ppm.

Although the invention has been described with respect to a preferred embodiment in the accompanying drawing, it is to be understood that the scope of the invention is not limited to such an embodiment.

Thus, for example, the embodiment may be modified in numerous ways within the spirit and scope of the present invention. Although it is preferred to provide AMS to the steam distillation column by retaining AMS byproduct in the crude phenol, as should be apparent, it is possible to add the AMS, and optionally, some cumene to the feed to the steam distillation column. In such a modification, the feed to the steam distillation column would still be under basic conditions.

As a further modification, crude phenol recovered from the cumene column 14 may be initially treated to separate heavier components therefrom, followed by the chemical treatment to reduce the quantity of acetol and MO.

As still another modification, the crude phenol may be chemically treated with a base in the cumene recovery column.

These and other modifications should be apparent to those skilled in the art from the teachings herein.

The invention will be described with respect to the following example; however, the scope of the invention is not to be limited thereby:

EXAMPLE

Crude phenol was purified in several stages as follows:
1. Treatment with hexamethylenediamine (HMDA)
2. Coarse Distillation
3. Azeotropic Distillation
4. Acid Treatment
5. High Purity Distillation

1. HMDA Treatment 20 grams of HMDA was added per gallon of feed and the mixture was agitated at 160° C. for two hours. pH of 5% aqueous solution of the above was 7.5.

2. Coarse Distillation

A column provided with 12 actual trays was used (feed on tray 2 from the bottom). The reflux ratio was of approx. 0.2/1.

| Pressure: | 100 mm Hg absolute |
|---|---|
| Temperatures: | Reboiler - 129–139° C. |
| | Overhead - 110–112° C. |

Of the material fed, 93.8% was recovered as overhead and 6.2% as residues.

3. Azeotropic Distillation

| Pressure: | Atmospheric |
|---|---|
| Temperatures: | Reboiler - 183–185° C. |
| | Overhead - 98–99° C. |

A column provided with 50 actual trays was employed. The feed was on the third tray from the top.

Water to phenol mixture ratio was 0.25 wt/wt. Of the total material fed, 73.4% was recovered as bottom products and 26.6% as overhead.

The overhead consisted of 18.6% of organic phase and 81.4% aqueous phase.

4. Acid Treatment

Two different acids were used.
a. Three grams phthalic anhydride per 1000 grams of feed, pH of 5% aqueous solution was 3.3.
b. Two grams of phosphoric acid was used per 1000 grams of feed, pH of 5% solution was 3.1.

5. High Purity Distillation

Two runs were made with phthalic anhydride treated (Run 1) and phosphoric acid treated (Run 2) phenol as feed.

| Pressure: | Overhead - 100 mm Hg | |
|---|---|---|
| | Reboiler - 125 mm Hg | |
| Temperatures: | Pasteurized Cut: | 110–112° C. |
| | Product Cut: | 111–112° C. |
| | Reboiler: | 122–125° C. |

The distillation column had 20 actual trays. The preheated feed was introduced on tray 5 (from the bottom). The pure phenol product was collected via a reflux splitter from tray 20. Above it, a short packed section allowed the pasteurizing cut to be removed overhead and condensed.

| Reflux Ratios: | Product Cut: | 1/1 |
|---|---|---|
| | Pasteurized Cut: | 25/1 |

Approximately 4% of the distillate was removed as pasteurized cut.

Samples in different stages of purification were analyzed by gas chromatography. Results are summarized in the following table.

PHENOL PURIFICATION

| Run Description | Sample Description | Acetone | MO | Acetol | Cumene | AMS | MBF | AP | DMPC | Unknowns | Phenol |
|---|---|---|---|---|---|---|---|---|---|---|---|
| | Crude Phenol | 97 | 74 | 2440 | 20015 | 23105 | 122 | 12035 | 730 | | |
| | HMDA Treated | 255 | 33 | — | 30427 | 27095 | 38 | 11169 | 430 | | |
| Azeo Still | Feed | 282 | 36 | — | 32095 | 27442 | 50 | 1768 | 299 | | |
| " | Bottom Product | 0.7 | — | — | 2.2 | 28.5 | 7.6 | 1308 | 105 | | |
| | OVHD (Org. Phase) | 2235 | 429 | — | 25.87* | 27.32* | 551 | 1448 | 87 | | 23.84* |
| | OVHD (Aq. Phase) | 795 | — | — | 152 | 263 | — | — | — | | 3.68* |
| High Purity Still (#1) | Feed | 4.0 | 0.6 | — | 2.3 | 29.7 | 7.3 | 1148 | — | | |
| | Product Cuts | 3.9 | — | — | 1.4 | 16.2 | 7.4 | 0.5 | — | | |
| | Pasteurized Cuts | 48.2 | 0.4 | — | 4.5 | 303 | 6.1 | 5.5 | — | | |
| High Purity Still (#2) | Feed | 18.0 | — | — | 2.5 | 25.8 | 10.8 | 1248 | — | | |
| | Product Cut | 6 | — | — | 2.0 | 18 | 5 | 1 | — | | |
| | Pasteurized Cut | 98 | — | — | 24 | 146 | 7 | 2 | — | | |
| | Reboiler Sample | | | | | | 7.59* | | | | |

*Concentrations in wt. %, all other figures are concentrations in ppm/

The present invention is particularly advantageous in that in a process for producing high purity phenol it is possible to effect steam distillation of phenol in the presence of AMS, without necessitating an increase in the phenol pasteurizing cut from the high purity column so as to reduce and/or eliminate the presence of AMS in the high purity phenol product. Thus, greater quantities of high purity phenol product are recovered in the sidestream from the high purity column by reducing the overhead pasteurizing cut. Thus, in accordance with the present invention, it is possible to retain the advantages resulting from the presence of AMS in the steam distillation column of a high purity phenol process.

Numerous modifications and variations of the present invention are possible in light of the above teachings and, therefore, within the scope of the appended claims, the invention may be practiced otherwise than as particularly described.

What is claimed is:

1. A process for producing high purity phenol, comprising:
    steam distilling in a steam distillation column a phenol product feed containing alpha-methylstyrene by-product and methylbenzofuran impurity to recover a light produce comprising phenol, water, alphamethylstyrene and methylbenzofuran, and a heavy product comprising phenol having a reduced quantity of MBF, said phenol product having been treated with a base without acidification; treating said heavy product with an acid; and distilling in a high purity phenol column the acidified heavy product to recover high purity phenol.

2. The process of claim 1 wherein the water to phenol ratio in the steam distilling is at least 0.05:1 and no greater than 0.8:1.

3. The process of claim 2 wherein the alphamethylstyrene is present during the steam distilling in an amount of at least 0.5% and no greater than 10%, by weight, based on phenol.

4. The process of claim 1 wherein the phenol product feed to the steam distilling is at a pH of at least 6.5 and the heavy product after treating with acid is at a pH of no greater than 5.5, all measured as a 5% aqueous solution.

5. The process of claim 1 wherein the base is an amine.

6. The process of claim 1 wherein the pH of the phenol product feed is at least 6.5 and no greater than 8.0 and the pH of the heavy product after treating with acid is no than 5.5 and no lower than 2.0, all measured as a 5% aqueous solution.

7. The process of claim 6 wherein the water to phenol ratio in the steam distilling is at least 0.05:1 and no greater than 0.8:1.

8. The process of claim 7 wherein the alphamethylstyrene is present during the steam distilling in an amount of at least 0.5% and no greater than 10%, by weight, based on phenol.

9. The process of claim 1 wherein said distilling of acidified heavy product recovers high purity phenol as a sidestream and an overhead of products lighter than phenol.

10. The process of claim 9 wherein the pH of the phenol product feed is at least 6.5 and no greater than 8.0 and the pH of the heavy product after treating with acid is no greater than 5.5 and no lower than 2.0, all measured as a 5% aqueous solution.

11. The process of claim 5 wherein the acid is selected from the group consisting of phthalic acid, phthalic anydride and phosphoric acid.

12. A process for producing a high purity phenol, comprising:
    steam distilling a phenol product feed containing alpha-methylstyrene in an amount of at least 0.5 percent, by weight, and methylbenzofuran impurity to recover a light product comprising phenol, water, alpha-methyl-styrene and methylbenzofuran, and a heavy product comprising phenol having a reduced quantity of methylbenzofuran, said phenol product feed having been treated with an amine base without acidification, said phenol product feed being at a pH of at least 6.5, measured as a 5% aqueous solution; treating said heavy product with an acid to provide a heavy product having a pH of no greater than 5.5; and distilling the acidified heavy product to recover high purity phenol.

13. The process of claim 12 wherein the pH of the phenol product feed is at least 6.5 and no greater than 8.0, and the pH of the heavy product after treating with acid is no greater than 5.5 and no lower than 2.0, all measured as a 5% aqueous solution.

14. The process of claim 13 wherein the acid is selected from the group consisting of phthalic acid, phthalic anhydride and phosphoric acid.

* * * * *